(12) United States Patent
Le Berre et al.

(10) Patent No.: US 10,471,430 B2
(45) Date of Patent: Nov. 12, 2019

(54) SUBSTRATE FOR SUPPORTING LIQUID SAMPLE, AN ASSEMBLY COMPRISING SUCH A SUBSTRATE AND USE THEREOF

(71) Applicant: ELVESYS, Paris (FR)

(72) Inventors: Maël Le Berre, Paris (FR); Adrien Plecis, Bourg la Reine (FR)

(73) Assignee: ELVESYS, Paris (FR)

( * ) Notice: Subject to any disclaimer, the term of this patent is extended or adjusted under 35 U.S.C. 154(b) by 0 days.

(21) Appl. No.: 15/759,218

(22) PCT Filed: Sep. 5, 2016

(86) PCT No.: PCT/EP2016/070805
§ 371 (c)(1),
(2) Date: Mar. 11, 2018

(87) PCT Pub. No.: WO2017/042115
PCT Pub. Date: Mar. 16, 2017

(65) Prior Publication Data
US 2018/0250670 A1    Sep. 6, 2018

(30) Foreign Application Priority Data
Sep. 11, 2015   (FR) ..................... 15 01889

(51) Int. Cl.
*G01N 21/01*    (2006.01)
*B01L 3/00*     (2006.01)
*G02B 21/34*    (2006.01)

(52) U.S. Cl.
CPC ............ *B01L 3/5088* (2013.01); *G01N 21/01* (2013.01); *G02B 21/34* (2013.01);
(Continued)

(58) Field of Classification Search
CPC ........... G01N 21/6428; G01N 21/6452; G01N 15/1475; G01N 33/54366; G01N 21/645;
(Continued)

(56) References Cited

U.S. PATENT DOCUMENTS 2,041,290 A    5/1936   Jackson
2,302,830 A    11/1942  Axelrad
(Continued)

FOREIGN PATENT DOCUMENTS

JP    2002 350305 A    12/2002
WO    82/02958 A1      9/1982
WO    2006/052492 A1   5/2006

*Primary Examiner* — Michael P Stafira
(74) *Attorney, Agent, or Firm* — Im IP Law; C. Andrew Im; Chai Im

(57) ABSTRACT

A micro-structured substrate to support a liquid sample having a lower face and an upper face. At least one surface cavity of volume V0 opening onto the upper face and forming a zone for analyzing the liquid sample. A first groove having a first volume V1, positioned around each surface cavity and opening onto the upper face thereof. The substrate also includes at least one second groove opening onto the upper face thereof and positioned around the first groove. The sum of the volumes of the second grooves is equal to V2. The volume V1+V2 is greater than or equal to 0.05 V0, preferably 0.1 V0. An analysis assembly including the substrate and the use thereof is also contemplated herein.

21 Claims, 4 Drawing Sheets

(52) U.S. Cl.
CPC . *B01L 2200/0684* (2013.01); *B01L 2300/089* (2013.01); *B01L 2300/0822* (2013.01); *B01L 2400/0406* (2013.01)

(58) Field of Classification Search
CPC ............. G01N 1/30; G01N 2021/0346; G01N 2030/8417; G01N 21/05; G01N 30/466; G01N 30/6095; G01N 30/82; G01N 33/53; G01N 33/543; G01N 33/54373; G01N 33/6803; G01N 33/6845; G01N 2015/1006; G01N 2015/1081; G01N 2021/058; G01N 21/6458; G01N 2500/10; G01N 27/27; G01N 2800/102; G01N 2800/105; G01N 2800/52; G01N 30/6091; G01N 33/491; G01N 33/5008; G01N 33/5044; G01N 33/54386; G01N 33/564; G01N 33/57415; G01N 1/36; G01N 1/42; G01N 21/253; G01N 21/6408; G01N 21/6486; G01N 21/658; G01N 2500/04; G01N 33/5088; G01N 33/5436; G01N 33/57492; G01N 15/1056; G01N 1/2813; G01N 1/286; G01N 1/312; G01N 1/38; G01N 2001/4027; G01N 2001/4088; G01N 2015/0084; G01N 2015/149; G01N 2021/3595; G01N 2021/6419; G01N 2021/6421; G01N 2021/6471; G01N 21/01; G01N 21/0332; G01N 21/3563; G01N 21/47; G01N 21/6456; G01N 21/65; G01N 2201/0636; G01N 2201/0675; G01N 2291/0423; G01N 2333/9015; G01N 2600/00; G01N 27/226; G01N 27/227; G01N 27/44756; G01N 27/453; G01N 29/222; G01N 33/48; G01N 33/50; G01N 33/502; G01N 33/5061; G01N 33/5082; G01N 33/545; G01N 33/574; G01N 33/582; G02B 21/34; G02B 2207/123; G02B 5/02; G02B 6/10; G02B 6/241; G01J 3/02; G01J 3/021; G01J 3/0229

See application file for complete search history.

(56) References Cited

U.S. PATENT DOCUMENTS

| | | |
|---|---|---|
| 4,882,245 A | 11/1989 | Gelorme et al. |
| 5,948,685 A | 9/1999 | Angros |
| 7,138,270 B2 | 11/2006 | Papkovsky et al. |
| 2003/0194709 A1 | 10/2003 | Yang |
| 2004/0202583 A1* | 10/2004 | Hower .................. B01L 3/5085 422/552 |
| 2004/0241783 A1* | 12/2004 | Papkovsky ......... B01L 3/50853 435/33 |
| 2011/0159547 A1 | 6/2011 | Yu et al. |
| 2012/0004139 A1* | 1/2012 | Staker .................. B01L 3/5027 506/16 |
| 2014/0106395 A1 | 4/2014 | Fattinger et al. |

* cited by examiner

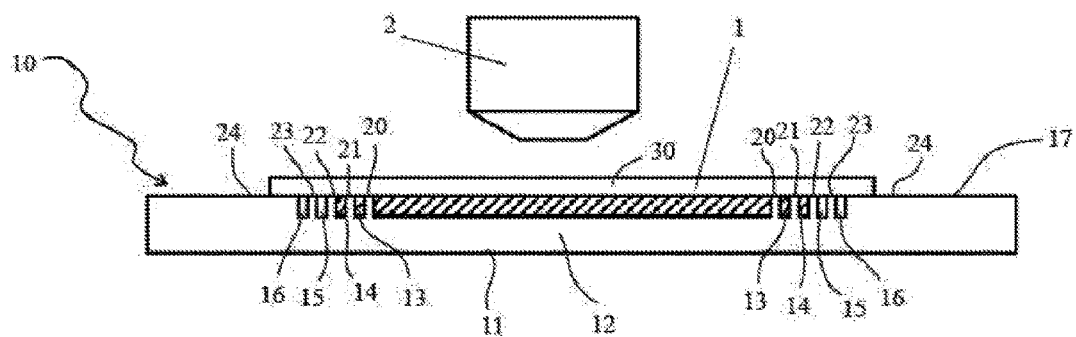
Fig. 1
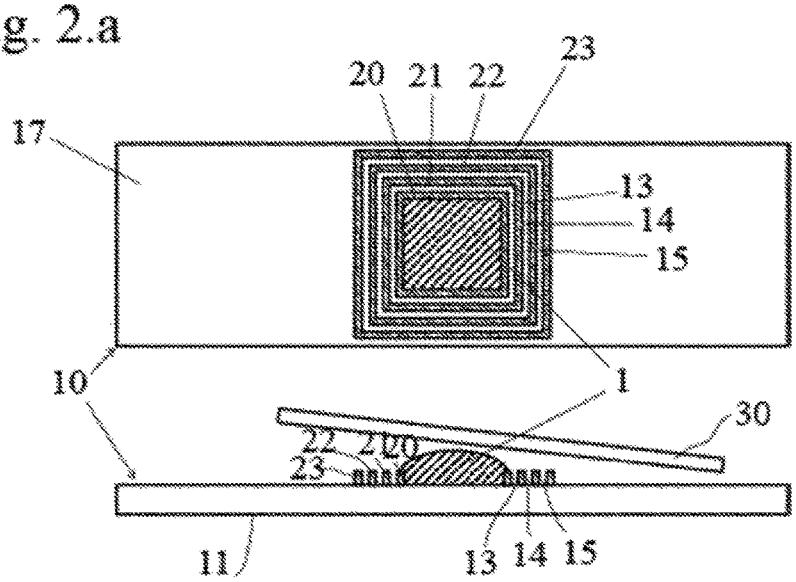
Fig. 2.a

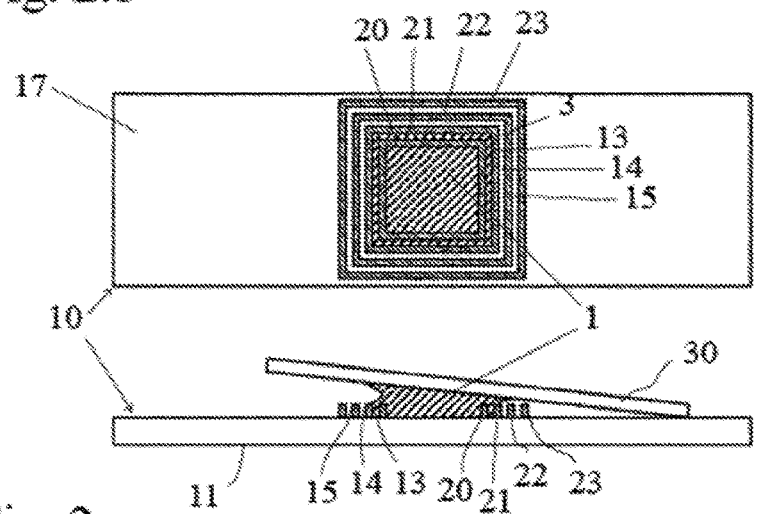
Fig. 2.b
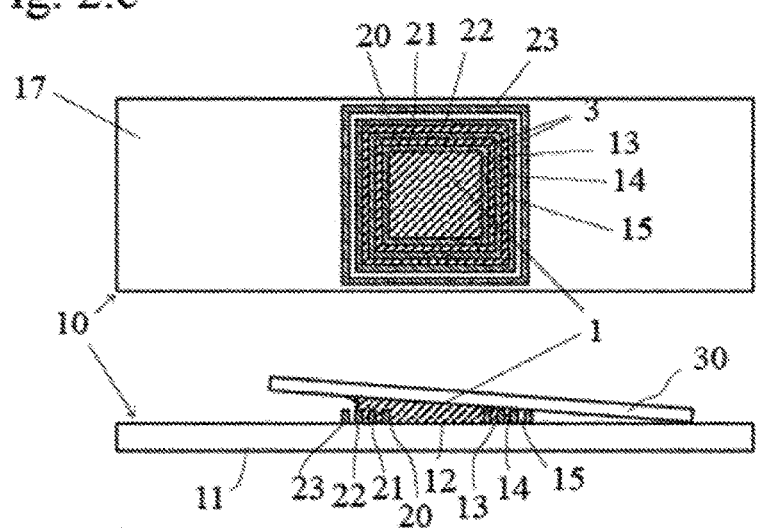
Fig. 2.c
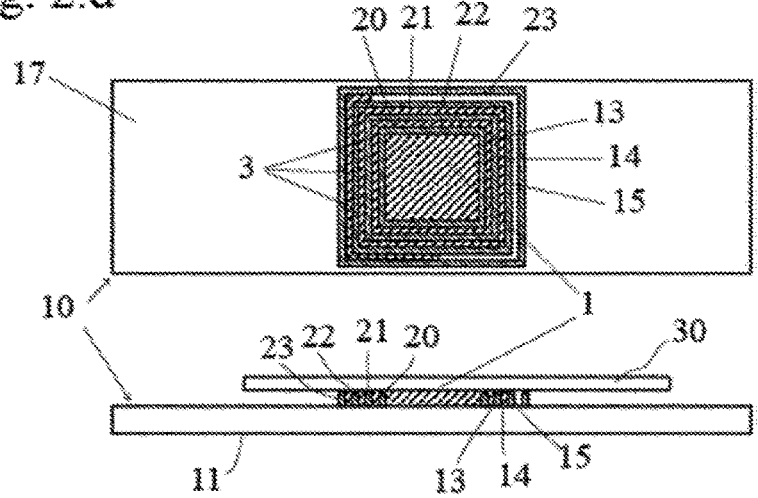
Fig. 2.d

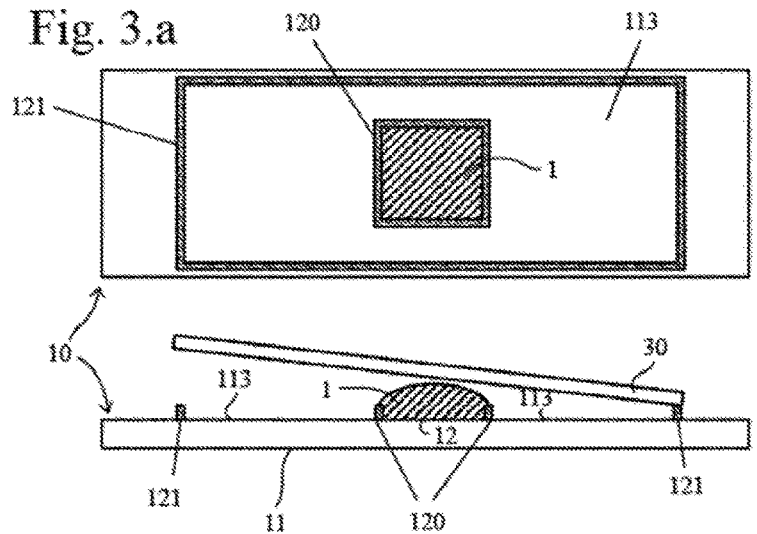
Fig. 3.a
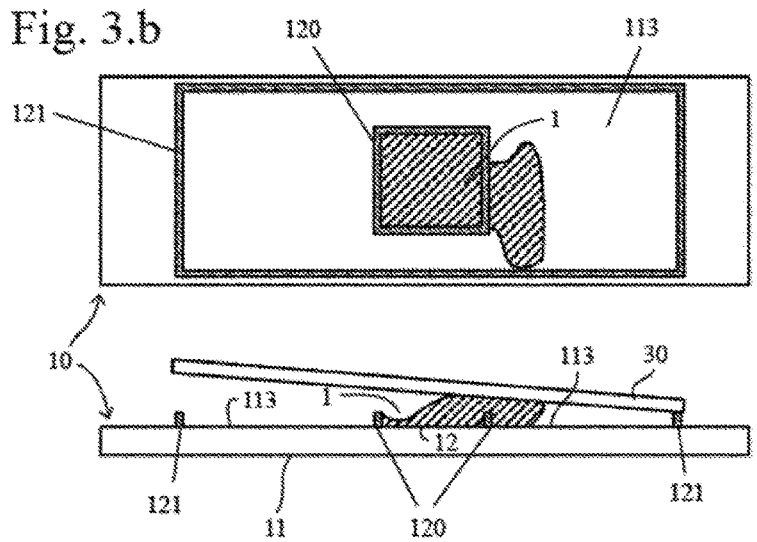
Fig. 3.b
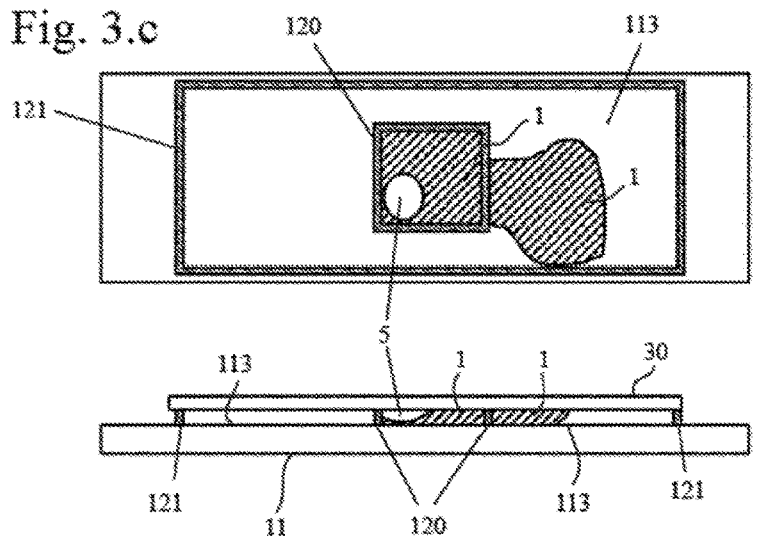
Fig. 3.c

SUBSTRATE FOR SUPPORTING LIQUID SAMPLE, AN ASSEMBLY COMPRISING SUCH A SUBSTRATE AND USE THEREOF

RELATED APPLICATIONS

This application is a § 371 application from PCT/EP2016/070805 filed Sep. 5, 2016, which claims priority from French Patent Application No. 15 01889 filed Sep. 11, 2015, each of which is incorporated herein by reference in its entirety.

FIELD OF THE INVENTION

The invention relates to a micro-structured substrate for supporting a liquid sample, said substrate comprising a lower face and an upper face which comprises, on the one hand, a surface cavity having a volume V0 opening onto said upper face and forming an analysis zone for the liquid sample and, on the hand, a first groove having a first volume V1 disposed around said cavity and opening onto the upper face thereof.

It also relates to an assembly for analyzing a liquid sample, said assembly comprising such a substrate, such as an assembly composed of a substrate, a liquid sample and a slide placed thereon, as well as a use of such a substrate for analyzing a liquid sample.

BACKGROUND OF THE INVENTION

In many research and analysis fields, the objective is to determine the presence or absence of some particles, so-called "particles of interest", in a liquid and/or to study the development of these particles of interest in this liquid and/or to promote the formation of structures from the particles in the liquid. These particles may be, on the one hand, biological objects such as cells (animal and/or vegetal, living and/or non-living cells), antibodies, proteins, viruses, etc. . . . and/or, on the other hand, non-biological objects such as molecules, so-called molecules of interest, including chemical molecules in particular polymers, liquids, etc.

Most of the protocols, implemented for the analysis and/or the study of a sample generally consisting of a liquid containing (or not) at least one particle, use a sample support which is frequently constituted of a parallelepipedic glass slide and an observation instrument such as a microscope, a spectrum analyzer, a fluorescence quantization system, etc. The sample is placed onto the glass slide, then a cover slip is gently placed onto the sample as illustrated in FIGS. 3A to 3C in the present specification, so as not to enclose air bubbles between the lower surface of the cover slip and the sample nor to damage the particles possibly present in the sample, the cover slip being then maintained by capillarity on the glass slide. In some applications, the cover slip can be fixed to the glass slide by adhesive bonding, generally with the help of wax, in particular in order to enclose the sample and avoid the evaporation thereof which may occur during continuous observations especially of long duration and/or when the sample is subjected to temperature variations, in particular temperature rises.

When limiting the evaporation of the liquid, the adhesive bonding technique makes it possible, on the one hand, to avoid or limit the movement of the liquid in the analysis zone of the sample and, on the other hand, to avoid a variation in the concentration of particles and/or salts possibly dissolved in the sample, which allows an observation of the particles under stabilized conditions.

However, the use of this type of protocols causes many difficulties for the user. First, when the liquid is deposited onto the slide, the drop can spread in an uncontrolled manner on the surface into a film a few microns thick. In addition to the sample loss along the edges of the blade, it then becomes difficult to control the lateral extension of the liquid, for example relative to an analysis zone imposed by the analysis instrument.

Other capillary phenomena can also disturb the positioning of the sample: when the cover slip is placed, it is common that the affinity of the liquid for one of the two substrates causes the drop to quickly migrate to one of the edges of the slide and the cover slip. This phenomenon is also at the origin of the wasting of a part of the sample and makes the positioning of the sample in the center of the cover slip more complex. The sample then gets a random lateral extension, and therefore has a thickness difficult to control. Finally, the presence of liquid at the edge of the cover slip can disrupt the adhesive bonding step which makes it possible to make the system hermetic. Since this step depends on the dexterity of the user, the result of conditioning the sample in the form of a thin cavity is very random and this can result in a large variability of the analysis results. The presence of liquid outside the slide and/or cover slip, which can thus be in contact with the user and/or the analysis instrument, is generally considered unacceptable particularly in the case of samples containing carcinogenic or toxic products.

Finally, the adhesive bonding step take a particularly long time to get implemented and requires the intervention of an experienced user. For this reason, this step is not possible for certain applications that require the analysis of a large number of samples. In addition, it does not allow the user to recover her/his sample since this type of adhesive bonding is not suitable for a reversible opening. In an attempt to find a remedy for some of these disadvantages, various solutions have already been proposed.

U.S. Pat. No. 2,041,290A discloses a sample holder in the form of a plate for the analysis of a liquid sample, for example a drop of blood, on the upper surface of which a plurality of circular wells is provided, each well being surrounded by a channel for collecting the excess of liquid from the sample to be analyzed in said well.

U.S. Pat. No. 2,302,830A discloses a plate of the same type in which the well is formed by depositing a circular bead of material onto the surface of the slide, this bead being surrounded by a circular groove etched in the surface of the slide so as to collect the excess of liquid to be analyzed.

U.S. Pat. No. 5,948,685A proposes to use a device consisting of a microscope glass slide on which a retention barrier less than 1 µm thick is structured for providing a well in the surface of the slide. As the sample is placed inside this well, any overflow is in principle stopped, which makes it possible to avoid the effects of loss of liquid at the edges of the cover slip. However, it has been found that, if the volume of the sample is poorly controlled, i.e. it is too big, this barrier is not sufficient to prevent it from leaking at the edges. In addition, if the cover slip that is just placed on the sample has a high affinity with the liquid sample, which is often the case and if it is not deposited strictly parallel to the slide, a liquid overflow event takes place along this cover slip.

WO 82/02958 discloses a support plate for the analysis of liquid samples, this pate comprising a plurality of assemblies for depositing a drop of liquid sample, each assembly being composed of a central well surrounded by a channel or groove capable of receiving the excess liquid deposited in the central well.

U.S. Pat. No. 7,138,270B2 describes in particular in FIG. 8 a support for liquid samples comprising a plurality of circular wells regularly distributed on the upper surface of the support. The typical height of the side walls of the wells is between 30 and 200 µm, all of these wells being surrounded by an external retention barrier. This type of configuration makes it possible to completely fill the wells with the help of an excess of liquid which is removed during the placement of the upper cover slip, in the intermediate zone situated between the different wells and delimited, on the one hand, by the lateral walls of the various wells and, on the other hand, by the external retention barrier. This external barrier makes it possible to retain the excess liquid to avoid any leakage outside the slide and the cover slip. In this type of system, the positioning of the excess liquid is however not controlled and it is necessary to deposit the cover slip in a suitable manner so as to limit cross contamination between the wells. Indeed, as long as the upper plate is not hermetically sealed to the structures of the wells, some of the excess liquid can be drained by capillarity out of a well in an uncontrolled manner. This has the effect of generating a bubble within one or more wells (if the amount of liquid drained is too great) and the diffusion of the particles from one well to another when the liquids overflowing from two consecutive wells mix to one another, thus contaminating the subsequent analysis of initially independent wells. In addition, the slightest dust or particle from the sample coming between the barrier and the upper cover slip or the slightest irregularity in the barrier is at the origin of a preferred non-controllable evaporation zone which limits the reproducibility of the analysis, especially when the latter takes time and requires to be performed at high temperatures. This configuration is therefore unreliable for routine analysis even if it is performed with particularly reproducible (and therefore expensive) technologies.

In order to limit the problems of evaporation and leakage, it has been proposed in WO 2006/052492A1 to first deposit a layer of rough glue on the retention barrier. The disadvantage of this solution is the impossibility to recover the sample, the loss of performance of this type of device in case of dust or defects in the manufacturing process and especially the risk of diffusion of the glue compounds in the sample to be analyzed which would then be contaminated.

US 2003/0194709A1 describes a method for producing a substrate comprising electrodes of hydrophilic material partially surrounded by hydrophobic zones in order to perform an electrochemical analysis of a DNA-type sample. The use of such a substrate does not require the use of a protective cover slip deposited on the liquid sample, this cover slip being used only for carrying out optical analyzes of a sample. Thus, the problem associated with the presence of an air bubble cannot exist with this type of substrate which is used without any cover slip.

None of the above-mentioned systems therefore makes it possible to provide a satisfactory solution to the problem of positioning and maintaining a liquid sample in a fine cavity, which allows precise lateral positioning of the sample, an excellent fluidic and chemical stability of the sample in the measurement area, as well as an absence of cross-contamination in the case of positioning multiple samples on the support, regardless of the user's dexterity and the accuracy of the sample volume.

Furthermore, when the supports such as described above are used with a cover slip (usually made of transparent glass or any other similar material) which comes to rest on the liquid sample in order to trap it between the cavity and the cover slip, so as to obtain an observable sample directly above the cover slip, it is very common to note that a gas bubble was formed in the liquid at the cavity, under the cover slip. The presence of this bubble that can move throughout the cavity makes the observation of the liquid sample difficult if not impossible, especially when the surface occupied by the bubble is large relative to the surface of the cavity. In an attempt to avoid the formation of this bubble due to a lack of liquid in the cavity, the experimenter tends to provide a substantially greater quantity of liquid relative to the volume of the cavity. However, it was found that this did not prevent the formation of this bubble when placing the cover slip onto a support such as described above.

OBJECT AND SUMMARY OF THE INVENTION

An object of the invention is a substrate of the micro-structured type which does not have the disadvantages of the supports of the prior art and makes it possible in particular to avoid the formation of a bubble in the liquid sample when closing the cavity of the support with a cover slip after depositing the sample in the cavity.

The micro-structured liquid sample support substrate according to the invention, which comprises a lower face and an upper face, which comprises, on the one hand, at least one surface cavity of volume $V0$ opening onto said upper face and forming an analysis zone for the liquid sample and, on the other hand, a first groove having a first volume $V1$, arranged around each surface cavity and opening onto said upper face is characterized in that it further comprises at least one second of groove opening onto its upper face and arranged around the first groove, the sum of the volumes of the seconds grooves being equal to $V2$, the volume $V1+V2$ being superior or equal to $0.05\ V0$, preferably $0.1\ V0$, the depth of the grooves being superior to 10 microns and inferior to 500 microns, preferably between 20 microns and 500 microns, the grooves being continuous and/or not in communication with one another.

According to a first variant, the volume $V1+V2$ is superior or equal to $0.2\ V0$, more preferably superior or equal to $0.3\ V0$.

According to another variant, the substrate according to the invention is characterized in that it comprises in total n grooves, with $n>2$, each groove of rank p superior or equal to 2 and inferior or equal to n being arranged around the groove of rank $(p-1)$, the total volume $V3$ of the $(n-1)$ first grooves being inferior or equal to $0.05\ V0$.

According to a preferred embodiment, the substrate according to the invention will have n grooves, n being inferior or equal to 100, preferably inferior or equal to 10.

According to a first alternative, the section of each of the grooves will be substantially identical and/or preferably constant or substantially constant: the substrate will comprise, for example, concentric circular grooves of the same section, preferably arranged at equal distances from one another.

According to another alternative, the section of at least one of the grooves, preferably the nth or last groove (the outermost one) will be superior to that of the other grooves, preferably superior or equal to 5 times, more preferably 10 times the section of the $(n-1)$th groove. The additional advantage of an nth groove having a volume substantially superior or much more superior to that of the $(n-1)$th groove, is to avoid, in the vast majority of cases, an overflow of sample liquid beyond of this nth groove, in particular in the case of a support comprising a plurality of cavities, each of them being surrounded by a plurality of grooves, for example the same number n of grooves.

According to a preferred embodiment, the substrate according to the invention comprises at least six, preferably at least eight surface cavities, each cavity having a diameter of about 5 mm and a depth between 20 microns and 500 microns and being distant of about 5 mm from another cavity, each cavity being surrounded by a series of 5 to 10 grooves of about 100 microns in depth, distant from one another by about 100 microns.

It has been found that it is important that the grooves are continuous and/or do not (fluidly) communicate with one another in order to avoid any capillary flow between the grooves and consequently the formation of bubbles in the central cavity.

In general, it has indeed been found that the presence of at least one second groove, which is continuous (and/or does not fluidly communicate with the other grooves) and disposed around the first groove, made it possible to ensure a regularly distributed flow (over 360 degrees) of the liquid from the cavity to at least the second groove, thereby avoiding the "wedge effect" when closing the cavity with a cover slip. Indeed, we have been able to observe that the abrupt capillary suction of the liquid of the sample in a groove could cause in certain cases a bubble in the more interior groove. The presence of at least one second groove prevents this bubble from appearing in the cavity, or observation zone of the sample. Moreover, by avoiding a sudden and therefore uncontrolled suction effect of the liquid, which causes too much flow of liquid, the presence of multiple grooves thus avoids emptying the cavity and causing the appearance of an air bubble under the cover slip.

Preferably the distance between the first groove and the second groove will be substantially constant (for example in the case of a first circular groove, the second groove will preferably also be circular, the two grooves being concentric). This further improves the results obtained.

Preferably also, these grooves without having necessarily an exactly constant cross-section all together, will generally have a substantially constant section so as not to create and/or favor privileged passages for the liquid during the flow thereof from the cavity to the first groove and from the first groove to the second groove, favoring the symmetry of the cavity and groove assembly.

The shape of the cavity, in particular the shape of the contour of the cavity, when opening onto the upper surface of the support, may be arbitrary, but will preferably be that of a bowl the walls of which are preferably substantially vertical or inclined towards the interior of the cavity and the contour of which will preferably be substantially symmetrical with respect to an axis perpendicular to the (generally flat) upper face of the support. The preferred contour will be circular, rectangular or square. Preferably, at least the first groove will have the same shape as that of the contour of the cavity, positioned substantially equidistant therefrom.

According to another variant, the surface on the upper face of the substrate between the contour of the cavity and the inner contour of the first groove will preferably be a flat or substantially flat surface, preferably oriented parallel to the lower face of the support, which is itself generally flat. This surface (hereinafter referred to as the first surface) may either retain its surface properties (for example hydrophilic or hydrophobic) inherent to the shape initially chosen for this surface and/or to the material used for the substrate or its upper layer (see below, for example, the case of the substrate the cavity and barriers of which are created by selective deposition of a layer of material), or be specially treated to give it different surface properties relative to the material used (for example, make it hydrophilic if it is hydrophobic or vice versa, or reduce and/or increase its hydrophilic or hydrophobic character).

The treatments to be applied to a surface in order to modify its surface characteristics with respect to the different liquids present in the samples to be analyzed (whether these treatments are of a physical and/or chemical nature) are generally known to those skilled in the art.

Of course, and according to yet another variant of the invention, it may also be necessary to modify the surface condition of one and/or several of the walls and/or wall portions of one or several of the grooves in a manner similar to that described above relating to the surfaces between the grooves (including the central cavity) so as to modify, if desirable, the surface condition of a portion of at least said surfaces. It is also possible to modify the shape of any surface or surface portion of the substrate intended in particular to be in contact with the liquid sample in order to modify its capillary properties, in particular the contact angle of the liquid with said surface. It is also possible according to another variant of the invention to modify the shape of the walls of the grooves and of the central cavity, in particular at the edges at the intersection of the upper face of the substrate and the side walls of the grooves or the central cavity so as to create additional capillary barriers, the effect of which will be added (in more or less) to the capillary barrier effect inherent to the initial shape of the surface and/or the material this surface is made of, with respect to the liquid of the sample. Throughout the present description, the term "capillary barrier" will be used to refer to any deformation of the surface or a surface portion of the substrate intended in use to be in contact with the liquid of a sample, whether this deformation results from a treatment of the surface and/or a modification of the shape of the surface, in particular the appearance of convex shapes thereon.

Thus, according to a variant of the invention, the support is characterized in that at least certain areas of the upper face and/or the cavity and/or the grooves are treated so as to modify in these zones the properties of the capillary barrier inherent to the surface condition of the support material and/or the geometry of the grooves and surfaces.

The section of the grooves may be arbitrary but will be, in different preferred variants, preferably rectangular, square, trapezoidal, triangular, etc.

In particular, it is possible to choose the shape of the section of a groove according to the value of the (convex) angle between the side wall of the groove and the surface of the upper face at the substrate (value of the convex angle of the edge) so as to modify the capillary barrier created by this convex surface which connects the grooves (or cavity) to the upper face of the substrate.

The convexity zone at each capillary barrier and in particular each edge is characterized by a convexity angle Alpha c defined as the angle between the local direction of the surface after the convexity zone (for example the lateral wall of a groove) and the overall direction of the surface (for example the direction of the upper face of the substrate). It has thus been found according to another variant of the invention that the capillary barrier thus created was particularly effective if Alpha c were such that:

$$\text{Alpha } c > 140° - (\text{Alpha } m \text{ support} + \text{Alpha } m \text{ surface})$$

and preferably, $$\text{Alpha } c > 180° - (\text{Alpha } m \text{ support} + \text{Alpha } m \text{ surface})$$

Alpha m support designating the wetting angle of the sample liquid on the surface of the cover slip that has just been deposited onto the liquid sample in the surface cavity of the support according to the invention (also called slide).

Alpha m surface designating the wetting angle of the sample liquid on the convex surface containing the capillary barrier.

Such a capillary barrier may take for example one of the following forms:

a groove etched in the glass by hydrofluoric acid lithography and having vertical sides (thus forming a convex zone at its inner edge having a convexity angle of 90°), and then treated with a hydrophobic surface treatment so as to have a wetting angle of contact of the water on the glass >70° so that the angle of the surface be on the inner side of the groove. In this case, the support surface may be a clean cover slip (wetting angle of about 20° for pure water and clean glass).

a resin structure of the epoxy type "novolac" marketed under the name "SU8" in the form of a wall defined by photolithography on a cover slip, and having vertical flanks. This type of surface can also form a capillary barrier with a clean cover slip (the SU8 resin having a wetting angle of about 70°).

a rounded valley molded in a polyolefin such as polyethylene whose inner side forms an angle (Alpha c) of 70° relative to the surface (thus easy to mold or form for example by embossing). This surface type can also form a capillary barrier with a clean cover slip slide (the PE having a wetting angle of 96°).

grooves etched by micro-machining in a surface of polytetrafluoroethylene (PTFE) or its derivatives or similar fluoro compounds having similar properties, with sides having a convexity angle of 135°. This type of surface can form a capillary barrier for any surface with water, but also for many other liquids.

advantageously, the convex zone may contain an edge defining the convexity angle in a accurate and well localized manner.

advantageously, the surface after the convex zone may be locally more hydrophobic (less wetting) for increasing the efficiency of the capillary barrier while having the free choice of the nature of the surface of the remaining surface, in particular the sample cavity (surface treatments for promoting the adhesion of the adhesive cells, for example, are often hydrophilic, so it may be necessary to keep a hydrophilic surface for that area).

In general, the material for the support may not only be glass usually used for these analysis plates but may also be constituted by any thermoplastic, thermosetting, transparent or not material as well as ceramic or other materials.

The dimensions of the grooves can be very varied according to the intended use of the support. The width and depth of the grooves may vary between 10 microns and 500 microns, preferably between 20 microns and 500 microns.

Preferably, the distance between the inner contour of a groove and the outer contour of the preceding surrounding groove and/or the cavity is between about 1 micron and 1 mm, preferably about 100 microns.

According to a first variant, the substrate is composed of a monolayer or multilayer material in which at least one of the grooves and/or the cavity is etched or thermally, mechanically and/or chemically formed.

According to a second variant, the substrate is composed of at least one first lower layer on which a second upper layer is deposited from which the side walls of the cavity and/or grooves are formed whose side walls are thus arranged in protrusion with respect to the lower layer. According to this variant, the grooves may be made by selective deposition of at least one resin or by vacuum deposition of PVD, CVD, PECVD type etc.

Local treatment of certain portions of grooves and/or cavity or the surface of the substrate to make these portions more or less hydrophilic or hydrophobic can be achieved by any means well known to those skilled in the art.

The grooves and/or cavity can be made without any particular problem: it is sufficient to use the well-known and identified forming methods for the material used: mechanical and thermomechanical forming, chemical etching (selective etching with the help of a masking technique), laser etching, as well as all techniques of selective deposition of materials onto a support when the cavity and/or grooves are created by a deposition technique (coating for example through a silk screen, chemical deposition, vacuum deposition of CVD, PVD, type etc.).

Of course, when the cavity and/or the grooves are created by depositing a material onto a support, the cavity and/or the grooves are not created by removing material on and from the upper surface of the support but by supplying a material identical to or different from that forming the support so as to create physical barriers delimiting the cavity and/or the peripheral grooves. For the sake of simplification, the terms cavity and groove will be used to denote respectively the volume within the first physical barrier (which is therefore continuous in this variant) and the volumes between the other barriers around the first barrier and thus around the central cavity (this variant is illustrated in particular in the Figures below).

It has generally been found that, with the micro-structured support according to the invention, the spreading zone 3 for the liquid sample 1 respects the envelope delimited by the grooves, thus making it possible to center the sample in a selected and non-random analysis zone and also limiting the risk of loss of sample leakage.

The preferred structures of the support according to the invention include the structures comprising two or three grooves around the central cavity, these grooves preferably being similar, i.e. preferably having the same cross-section, as well as the structures in which the last groove has a larger section than the other grooves.

The invention also relates to an optical analysis assembly for a liquid sample, characterized in that it comprises a substrate 10 as defined above, on which at least one liquid sample 1 is deposited in at least one cavity 12 of the substrate 10, the volume of the sample 1 being superior to the volume of the cavity 12, the substrate 10 being covered by a cover slip 30 closing all the cavities 12 of the substrate 10.

In order to achieve with the substrate according to the invention a good optical analysis of the sample as explained in the present application, it is indeed important to avoid the formation of an air bubble in the liquid sample: for this purpose, it is especially necessary that the volume of the liquid sample placed into the cavity be preferably slightly superior to the volume of the cavity without however flowing over this cavity thanks to the meniscus of liquid forming at the top of the cavity. For this purpose, it is necessary that the manipulator be well trained or it will be necessary to have an automated system for supplying a calibrated volume, theses systems being commercially available such as automatic pipettes. As a general rule, it is considered that the volume of the grooves must preferably contain the excess volume of liquid in the central cavity when a cover slip is placed on the substrate.

According to one variant, at least one of the intersections between the lateral surfaces of the grooves 13, 14, 15, 16 and/or the cavities 12 and the upper surface 17 of the substrate 10 is a convex surface or surface portion whose convexity angle Alpha c, defined as the angle between the local direction of the lateral surfaces of the grooves 13, 14, 15, 16 and/or the cavities 12 and the direction of the upper surface 17 of the substrate, is such that:

Alpha c>140°−(Alpha m support+Alpha m surface)

and preferably,

Alpha c>180°−(Alpha m support+Alpha m surface)

Alpha m support designating the wetting angle of the sample liquid 1 on the surface of the cover slip 30 that has just been deposited onto the liquid sample 1 in the surface cavity 12 of the support 10.

Alpha m surface designating the wetting angle of the sample liquid 1 on the convex surface or surface portion connecting the grooves or cavities on the upper surface 17 of the substrate 10.

In general, the grooves will be continuous and separated from one another. Although it is possible to make two or several wells and/or grooves communicate with one another and in particular several wells with one another and to provide an assembly of grooves surrounding the plurality of wells (as represented for example in FIG. 6 of the present application where the grooves are common to several cavities), it will be preferable not to provide liquid communication between the different grooves, with one another and/or with at least one cavity.

The substrate defined above as well as the analysis assembly find their use especially for analyzing a liquid sample, in particular in using the so-called amplification technique "PCR" (or "Polymerase Chain Reaction").

BRIEF DESCRIPTION OF THE DRAWINGS

The invention will be better understood with the help of the following non-limiting exemplary embodiments in conjunction with the Figures in which:

FIG. 1 is a schematic view of a system composed of a micro-structured substrate according to the invention covered with a plate during an analysis of the microscopic observation type.

FIGS. 2A to 2D are schematic views of the steps of filling the micro-structured zone of the substrate according to the invention.

FIGS. 3A to 3C are schematic views of steps of filling a substrate of the prior art.

DETAILED DESCRIPTION OF THE EMBODIMENTS

Figure 4:
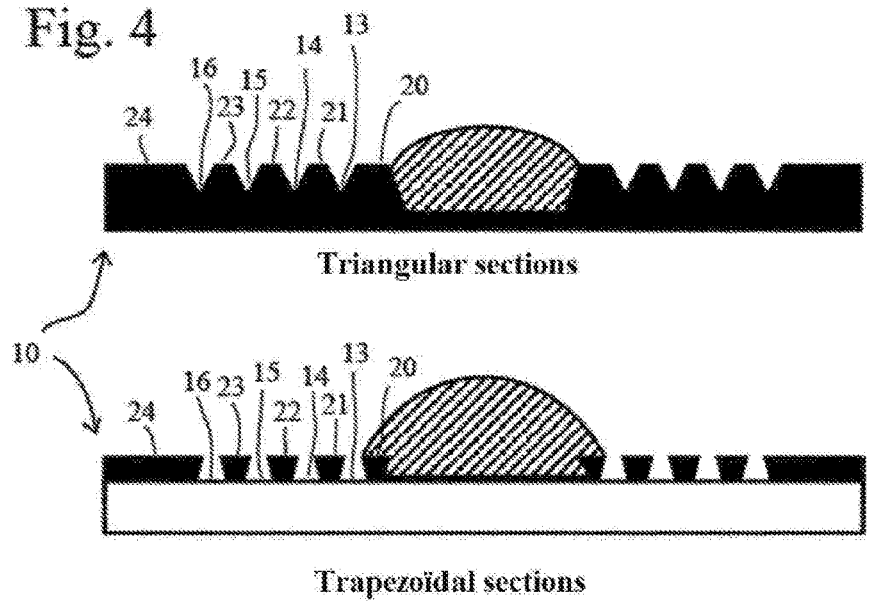
FIG. 4 are schematic examples of outlet networks (grooves) of triangular and trapezoidal sections.

In all the Figures, the same elements have the same references.

FIG. 1 is a schematic sectional view of an exemplary embodiment of the support according to the invention in end use in which is represented a schematic sectional view of the assembly according to the invention consisting of a micro-structured substrate 10 composed of a thick material having a lower face 11 and an upper face 17 onto which opens a network of surface cavities. This network of surface cavities is composed of a first surface cavity 12, called "analysis zone", for receiving the liquid sample 1 to be analyzed, above which is placed, according to the present example, a conventional microscopy system via a microscope objective 2. The network of surface cavities further comprises a plurality of grooves 13, 14, 15, 16 forming a zone, called "outlet zone", for collecting the excess sample 1 initially deposited by the user into the analysis zone and/or during the placement of the transparent plate 30 onto the support at the analysis zone. The outlet zone consists of an assembly of grooves preferably in a concentrically arrangement when the central cavity 12 has a center of symmetry.

The grooves, hereinafter also called "outlet passages" are in this example four in number and such that the groove 16 surrounds the groove 15 which surrounds the groove 14 which surrounds the groove 13 which itself surrounds the central cavity 12 or analysis zone. The outlet passage 13 is hereinafter called "primary" outlet passage, i.e. surrounding only the cavity or analysis zone 12. (the other outlet passages 14, 15, 16 are hereinafter called "secondary outlet passages, i.e. surrounding the analysis zone 12 and the primary outlet passage 13). In this Figure, the sections of the grooves are substantially identical. In this example, the cavity and groove assembly are surmounted by a closing plate 30 composed of a microscope glass cover 150 µm thick, thus forming an assembly of non-related cavities. The cavity and groove assembly comprise similar or different separation surfaces 20, 21, 22, 23 (extended by a surface 24).

A method, for example, for producing a micro-structured substrate according to this figure consists in choosing for the thick material a microscope slide, for example of dimensions 26 mm×76 mm out of plastic material such as polystyrene, to apply a pressure with the help of a parallelepipedic metal part, on one of the surfaces of the slide which will be the upper surface 17 of the micro-structured substrate, the lower surface 11 being supported by a flat metal part preferably covering the entire substrate. By heating the two metal pieces to a temperature close to the glass transition temperature (95° C.) of the selected material and by applying onto the parallelepipedic metal a pressure superior to 1 bar, the latter will go down into the polystyrene cover slip a few tens of microns according to the time and the pressure exerted. After cooling the structure and separating the metal parts and the cover slip, a rectangular-shaped surface cavity is obtained on the upper surface of the cover slip constituting the analysis zone 12. This manufacturing method is generally considered to be a thermoforming method and it is compatible with most plastics and amorphous materials (such as glass, thermoplastic resins, etc.). In order to realize the concentric grooves 13, 14, 15, 16 in the outlet zone, one can for example repeat the operation with four metal parts of increasing rectangular sections positioned so as to form concentric grooves. For further details, see for example J L Throne, Understanding Thermoforming, Hans Gardner Publications, Inc., Cincinnati Ohio, 1999.

The nested structure of the grooves makes it possible to control the spreading zone of the liquid sample 1 between the micro-structured substrate.

Of course, one can achieve the same structure according to the invention by depositing the retention barriers 20, 21, 22 and 23 on a support and thus create a relief.

The convex surfaces formed by the edges delimiting the grooves 13, 14, 15, 16 form capillary barriers whose properties are inherent to the geometry and/or materials and surface treatments used to make the support. According to the invention, the properties of these capillary barriers can be modified by modifying the geometry of the grooves, and in particular of their edges and/or by locally (partially or totally) treating them and/or the surfaces surrounding them, as explained above.

FIGS. 2A to 2D schematically illustrate the steps of filling the cavity/surface groove assembly during the standard use by an experimenter, for example in biology. This example also illustrates another embodiment of a micro-structured substrate according to the invention, in which the network of surface micro-cavities is produced by a lithographic photo process as described, for example, in the book by Sami Franssila "Introduction to Microfabrication", Wiley in a layer of micro-structured material covering a plane thick material. This manufacturing method has the advantage, compared to the thermoforming technique described above, of allowing the combination of different materials in contact with the liquid sample 1.

In FIG. 2A, it is represented the first step of filling the fine analysis cavity: it corresponds to the deposition of the liquid sample 1 onto the micro-structured substrate. The user using for example a micropipette deposits a volume of liquid sample 1 superior to the sum of the volumes of the analysis zone 12 and the primary outlet passage 13. According to the affinity of the liquid for the material constituting the layer of micro-structured material, the lateral extension of the liquid sample is then either limited by the outer envelope of the analysis zone (negative capillary barrier or weak affinity), or by the inner envelope of the cavity forming the primary outlet passage 13 or first groove (positive capillary barrier or strong affinity).

To benefit from this retention effect, referred to above as the capillary barrier, the volume of liquid delivered by the user must remain below a critical volume, which depends on the affinity of the liquid sample for the layer of micro-structured material. In the case of an aqueous liquid sample 1, the use of a hydrophobic material such as an epoxy resin such as SU-8 resin (described as well as its implementation in U.S. Pat. No. 4,882,245) allows the improvement of the retention force of the liquid sample during the liquid distribution step and therefore the maximum volume delivered. In this case, the use of a hydrophobic resin of this type which, after elimination of the irradiated areas (central cavity and grooves) with the help of a UV source of appropriate wavelength, makes it possible to preserve the protected areas during the UV irradiation step, thus creating negative capillary barriers between the outer contour of the cavity and the inner contour of the first groove, between the outer contour of the first groove and the inner contour of the second groove, etc . . . , these negative capillary barriers, all of the same kind in this example, being the separation surfaces 20, 21, 22, 23, 24, and the convex surfaces of the edges of the grooves attached thereto.

The user then closes the assembly consisting of the micro-structured substrate, the liquid sample 1 and a cover slip constituting the closing substrate 30 in order to finalize the forming of an analysis assembly comprising the substrate 10, the liquid 1 to be analyzed and the closing cover strip 30. The evolution of the liquid sample 1 within the holding structure is repented successively in FIGS. 2B, 2C and 2D in which the progressive lowering of the cover slip 30 makes it possible to cause the liquid 1 to flow at least in the grooves 13 and 14, avoiding the formation of a bubble in the sample when the assembly is closed.

For a critical approximation of the closing substrate 30 and the micro-structured substrate 10, the excess volume of liquid sample becomes too large to remain above the analysis zone 12. The pressure exerted on the liquid by the closing substrate 30 then causes the liquid sample 1 to cross the capillary barrier attached to the surface 20 and fills the groove 13, which sharply reduces the amount of excess liquid sample. The spreading zone for the sample then covers the analysis zone and the primary outlet passage 13, the liquid being temporarily stopped by the new capillary barrier 21 between the primary passage 13 and secondary passage 14.

When the closing substrate is brought closer again (FIG. 2C), the compression of the excess volume reaches again a tipping point which allows the filling of the second groove 14 (or first secondary outlet passage). The successive filling of the nested secondary outlet passages results in the end in the formation of a thin cavity such as depicted in FIG. 2D in which, in this example, the last outlet passage 15 (third groove) is a priori only partially filled, according to the remaining excess volume just before the complete closure of the cavity 12. In some cases, the sudden filling of the last groove 15 to be filled can cause the appearance of a bubble in the previous groove 14. For this reason, it is important that there be at least two grooves around the sample area in order to avoid the appearance of a bubble in the central cavity 1. In these FIGS. 2A to 2D, a substrate with three grooves 13, 14 and 15, of substantially identical sections has been taken as an example.

Exemplary embodiments of the invention are described below.

EXAMPLE 1

In this example, the retaining substrate 10 consists of a silica glass microscope slide onto which has been deposited a micro-structured layer of photo-sensitive resin SU8 50 µm thick defining an analysis zone (cavity) 12 of total volume substantially equal to 5 µL on a circular surface of 1 cm$^2$ and surrounded by a series of two grooves, the first groove having a rectangular section 50 µm deep and 200 µm wide that is a volume of 0.4 (i.e. 0.08 times the volume of the cavity), the second groove having a depth of 50 µm and a width of 5 mm, that is a volume of 15 the two grooves and the cavity being respectively separated from one another by a distance of 200 µm. It can be seen that, in general, the repetition of the grooves according to the invention makes it possible to avoid the appearance of a bubble in the analysis zone for small volumes of liquid (5 µL) and for larger volumes (up to 20 µL in this example). The contact angle of the drop delivered into the analysis zone is superior to 70°, which characterizes a hydrophobic material (resin SU-8). This exemplary substrate according to the invention allows the precise positioning and the maintenance of a cavity-like analysis zone, without bubble, thereby preventing any overflow of the liquid sample outside the cavity of the micro-structured zone. This type of substrate makes it possible to control the thickness of the analysis cavity by controlling the height of the structured layer.

In this example, while the hydrophobic material constituting the structured layer makes it possible to retain a greater excess volume than in the case of a hydrophilic structured layer, the use of a hydrophilic thick material (a silica glass) makes it possible, on the other hand, to improve the filling rate for the successive grooves and thus minimizes the probability of bubble formation in the grooves during too fast a closure by the user. The filling of several grooves is particularly recommended to limit evaporation problems of the liquid sample in the analysis zone.

Indeed, the succession of grooves filled with the excess liquid is a barrier to evaporation all the more effective since the number of cavities and filling cavities is large. It is another advantage of the invention to use a plurality of grooves for obtaining a liquid barrier surrounding the analysis zone and thus preventing, as long as this liquid barrier is intact, evaporation from appearing in the analysis zone at the origin of fluidic or chemical instabilities.

EXAMPLE 2

The support of Example 1 was used to carry out exemplary experiments showing that the spreading zone for the liquid sample 1 on a substrate according to the invention is stable: the assembly formed by the support plus the liquid sample trapped by the cover slip 30 was warmed to 50° C. for 30 minutes: no significant evaporation of the liquid sample in the analysis zone was observed. It was not affected by the evaporation process. In comparison, in the case of a system formed by a slide and a cover slip without any microstructures, the same amount of liquid sample was completely evaporated after only 20 min.

The succession of grooves thus constitutes a barrier to evaporation and keeps the analysis zone intact.

Without wishing to be bound by any theory, the inventors believe that this effect can be attributed to the succession of evaporation pockets. Indeed, each groove, even empty, is a buffer zone in which the humidity can increase until saturation. In the case of a simple barrier, evaporation is all the more rapid in the analysis zone since the process is carried out by contact with the outside air directly. The slightest defect in the retention barrier or the slightest dust at this level also dramatically increases the evaporation of the liquid sample. In a system according to the invention, the multiplication of intermediate cavities between the analysis zone and the outside slows the evaporation process. When it is desired to benefit from this advantage linked to the slowing down of the evaporation of the liquid, use will preferably be made of a support provided with a plurality of grooves with n superior or equal to 3.

EXAMPLE 3

This example describes the production of a micro-structured substrate according to the invention comprising several surface cavities, each cavity being surrounded by a plurality of grooves (there is not necessarily, although it is preferred, the same number of grooves around each cavity). On a cover slip of usual format (2.54 cm×5.08 cm) for example of synthetic material of PS or PMMA type, two parallel rows of four circular wells (cavities) 5 mm in diameter and 25 microns deep (i.e. a V0 volume of 0.5 microliter) are produced by molding or stamping. Each well is distant from the previous well in the row by 5 mm (distance between the perimeters of the cavities). Each well is surrounded by a series of 5 to 10 grooves of 100 microns depth, 100 microns apart. A series of 5 grooves thus corresponds to a volume of 0.22 V0 and a series of 10 grooves corresponds to a volume of 0.48 V0.

This type of substrate enables to reliably deposit very small samples, without the presence of a bubble after recovering with the upper plate, without any risk of contact of the samples with one another, thereby limiting the evaporation that can be fast for these small volumes. This substrate makes it possible, in particular, to simultaneously observe several samples containing animal cells or yeast-type microorganisms, which have dimensions of between 2 and 20 microns.

FIGS. 3A to 3C illustrate an example of the filling process for the cavity with the aid of a liquid sample according to the prior art. A double retention barrier 120, 121 is used for the distribution of the liquid sample 1 and for any possible sample leakage. The gap 113 between the two retention barriers can be likened to a groove or primary outlet passage. The user deposits a volume of liquid superior to the volume limited by the retention barrier 120: the volume distributed being superior to the volume of the analysis zone, during the closure (FIG. 3B), the capillary barrier created by the retention barrier 120 is exceeded by the liquid sample 1. By capillarity, under the influence of the angle between the upper substrate and the lower substrate, an uncontrolled amount of the liquid sample is absorbed in the gap 113. "The wedge effect" between the closing substrate 30 and the micro-structured substrate causes the analysis zone to be emptied of a large part of the liquid sample. When the final cavity is closed (FIG. 3C), the analysis zone then comprises a bubble 5 due to the uncontrolled outlet of excess liquid. If the user provides a volume superior to the total volume of the analysis zone and the primary outlet passage, the liquid is then caused to pass the retention barrier 121: in addition to leakage problems outside the device, which represents a risk for the user and/or the instrument in the case of corrosive or carcinogenic samples, the uncontrolled outlet of liquid out of the device is at the origin of bubbles in the device and therefore in the analysis zone. In general, it has been observed that the suction of the liquid sample in a groove or "wedge effect" could often cause the appearance of a bubble in the innermost groove so that it is necessary to provide at least 2 grooves, that do not communicate with one another, to prevent a bubble from appearing in the central cavity, or observation zone for the sample, a bubble being able to appear in this area if there is only one groove. In the case of the invention (FIG. 1 and FIGS. 2A to 2D), it is however important to note that it is preferably necessary that the primary passage (the first groove) be completely filled before the outlet step to the secondary passages (second groove and subsequent grooves) to benefit from the best protection effect by the second groove. When positioning the closing cover slip, it is preferable to avoid too fast a movement or a sliding movement of the substrate 30 parallel to the micro-structured substrate, since this could cause the liquid to cross the surface 21 between the primary outlet passage 13 and the secondary outlet passage 14 before forming the negative capillary barrier on the surface 20 around the analysis zone 12. In this case, a bubble could be introduced uncontrollably into the analysis zone.

To eliminate this disadvantage, different variants are possible: the first solution is to reduce the volume of the first groove. The smaller this volume, the shorter the time to fill it and the lesser the user's dexterity comes into play in the constitution of the capillary barrier. In particular, when the volume of the primary passage 13 is at least 3 times, preferably at least 5 times and more preferably at least 10 times inferior to the volume V0 of the cavity 12, the filling time for the first groove 13 becomes negligible with respect to the user's action.

The second solution consists in using a volume distribution for the different cavities and grooves which ensure that the analysis zone cannot be emptied even in the absence of a complete negative barrier. Thus, if the volume of the primary outlet passage is smaller than the volume of the analysis zone and the volume of the adjacent secondary outlet passage, it is ensured that either (i) the liquid prefers the cavities of low volume (strong affinity of the liquid for the surface of the substrate) and in this case the primary passage will preferably be filled through the secondary passage, or (ii) the liquid prefers the cavities of the substrate of high volume (strong affinity of the liquid for the surface of the substrate) and in this case the primary passage will be preferentially emptied with respect to the analysis zone.

The third solution consists in accelerating the filling of the first groove by exploiting the materials inside the cavities and grooves. In the examples of FIGS. 2A to 2D, the glass used for the bottom of the cavity is hydrophilic, which has the effect of attracting the liquid more rapidly in the primary outlet passage than if the entire surface cavity had been made in a single hydrophobic material. On the other hand, the walls and the contact areas between the grooves must preferably remain hydrophobic, which makes it possible to improve the effect of capillary barrier when filling cavities. To improve the complete filling of a protective liquid barrier around the analysis zone, it is preferable that the hydrophilic surface portion in the primary outlet passage completely surrounds the analysis zone. Conversely, for an oil-type liquid, it is more advantageous to provide a primary outlet passage having a hydrophobic bottom and hydrophilic walls and contact zones.

It is important to note that for an extension and a given total volume of the outlet zone, the greater the number of outlet passage (preferably up to 5 grooves), the better the sample will remain correctly positioned, all other things being equal.

FIG. 4 shows schematically an assembly of grooves in the form of micro-channels of triangular sections (FIG. 4—top) or trapezoidal (FIG. 4—bottom). Indeed, the geometry of the various cavities and surface grooves constituting the micro-structured network of the support can be advantageously modified for the needs of the user. The more the spacing between the outlet passages is regular, the more the positioning will be reproducible. The use of an assembly of micro-channels of constant section for the outlet passages also makes it possible to obtain a homogeneous filling of the outlet zone and limits the filling errors related to a bad positioning of the closing substrate by the user. The use of surface cavities essentially composed of portions of rectangular sections makes it possible to obtain angle effects at the bottom of the cavities that facilitate and accelerate the filling of the outlet passages while limiting the appearance of bubbles. However, depending on the affinity of the liquid sample for the substrate, it will be possible to opt either for triangular-type sections that reduce the probability of bubble formation (liquids with low affinity for the micro-structured substrate) or for trapezoidal-type sections that increase the efficiency of the capillary barrier between the different cavities (liquids with high affinity for the micro-structured substrate).

FIG. 4 illustrates two schematic examples of outlet networks composed of micro-channels of thus-defined triangular and trapezoidal sections. It should be noted in these examples that the thickness of the surface cavities is not necessarily homogeneous. For example, the analysis zone may have a greater thickness than the outlet passages when it is desired to save the liquid sample to be analyzed while benefiting from a maximum of outlet passages for precisely positioning the sample. Conversely, deepening the outlet passages will store more excess liquid in order to slow down the evaporation process.

It is understood that several networks of surface cavities may be juxtaposed on the same substrate to provide a larger number of samples.

Figure 5:
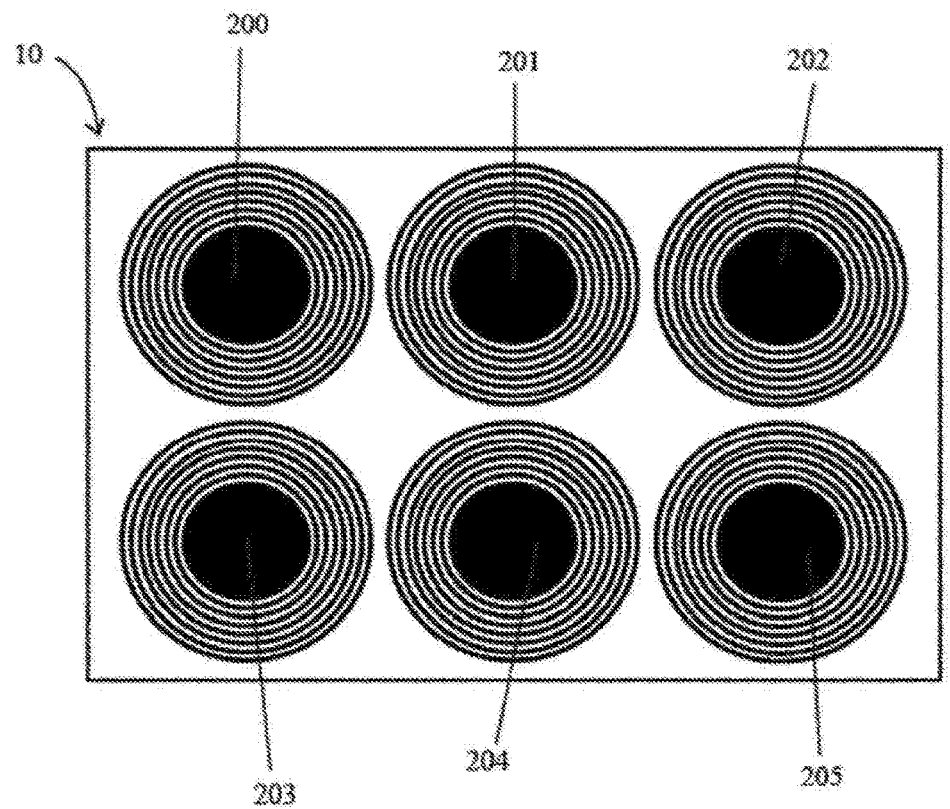
FIG. 5 is a schematic view of an exemplary substrate according to the invention for a multi-sample analysis.

FIG. 5 represents an example of a substrate according to the invention intended for a multi-sample analysis using surface cavities of circular lateral geometry. For each analysis zone 200, 201, 202, 203, 204, 205, an outlet network composed of a plurality of circular grooves arranged concentrically around each analysis zone, each network being independent and disjoined from the other networks, allows to limit the contamination of the samples by one another.

Conversely, the analysis zone can be organized as the juxtaposition of several zones.

Finally, it should be noted that the closing substrate (cover slip 30) or the micro-structured substrate, respectively, may be composed of any system that has a flat surface, or an upper surface, including an analysis surface (CCD sensor, etc.) or a control surface (micro-fluidic thermalization or infusion chip).

The system described by the invention can be used to position a biological sample in the form of a fine cavity before observation by optical microscopy. Another example of application consists in using the system of the invention for a biological detection system by interaction with objects distributed at the surface of the substrate (DNA or protein chip) in which the invention makes it possible to close the reaction chamber by ensuring a homogeneous reaction throughout the analysis zone. A third example of application is the systematic analysis of a chemical product by using an automatic dispenser coupled with a transmission analysis using a spectroscopy system for the fine cavity formed with the help of the invention without any leakage of the sample.

The invention claimed is:

1. A micro-structured substrate having a structure to support a liquid sample, comprising:
   a lower face;
   an upper face;
   at least one surface cavity, having a volume $V0$, opening onto said upper face and forming an analysis zone for the liquid sample;
   a first groove, having a first volume $V1$, arranged around each surface cavity and opening onto said upper face;
   at least one second groove opening on said upper face and arranged around the first groove;
   wherein a sum of volumes of the second grooves being equal to $V2$, a volume $V1+V2$ being greater than or equal to $0.05\ V0$, a depth of the first and second grooves being between 10 and 500 microns;
   wherein the first and second grooves are continuous and not in a fluid communication with one another; and
   wherein the structure of the micro-structured substrate prevents generation of bubbles when closing the cavities with a cover slip.

2. The micro-structured substrate according to claim 1, wherein the volume $V1+V2$ is greater than or equal to $0.1\ V0$.

3. The micro-structured substrate according to claim 1, wherein the depth of the first and second grooves is between 20 and 500 microns.

4. The micro-structured substrate according to claim 2, wherein the volume $V1+V2$ is greater than or equal to $0.2\ V0$.

5. The micro-structured substrate according to claim 1, wherein a total of first and second grooves is equal to n, with $n>2$, each groove with a rank p greater than or equal to 2 and less than or equal to n is arranged around a groove with rank p-1, and wherein a total volume of n-1 first grooves is greater than or equal to 0.05 V0.

6. The micro-structured substrate according to claim 1, wherein a total of first and second grooves is equal to n, n being less than or equal to 100.

7. The micro-structured substrate according to claim 1, wherein a total of first and second grooves is equal to n, n being less than or equal to 10.

8. The micro-structured substrate according to claim 1, wherein a section of each of the first and second grooves is substantially identical and constant.

9. The micro-structured substrate according to claim 1, wherein the first and second grooves comprise n concentric circular grooves of a same section.

10. The micro-structure substrate according to claim 9, wherein the n concentric circular grooves are arranged equidistant from one another.

11. The micro-structured substrate according to claim 1, wherein a section of at least one of the grooves is greater than a section of other grooves.

12. The micro-structured substrate according to claim 1, wherein the nth or an outmost groove is greater than a section of (n-1)th groove.

13. The micro-structured substrate according to claim 12, wherein the nth or outmost groove is greater than or equal to 5 times that of the section of $(n-1)^{th}$ groove.

14. The micro-structured substrate according to claim 1, wherein a distance between an inner contour of one groove and an outer contour of a previous surrounding groove or the cavity is between 1 micron and 1 mm.

15. The micro-structured substrate according to claim 1, wherein at least an area of the upper face, the cavity and one of the grooves are treated to modify, in the treated zones, at least one of properties of a capillary barrier inherent to a surface state of a material of the micro-structured substrate and a geometry of the grooves and surfaces.

16. The micro-structured substrate according to claim 1, further comprising at least six surface cavities, each surface cavity having a diameter of 5 mm and a depth between 20 and 500 microns and being spaced from another cavity by 5 mm, wherein said each surface cavity is surrounded by a series of 5 to 10 grooves of 100 microns in depth, spaced apart from one another by 100 microns.

17. The micro-structured substrate according to claim 1, wherein the micro-structured substrate is constituted by a mono-layered or multi-layered material in which at least one of the grooves and the cavity are either etched, or thermally, mechanically or chemically formed.

18. An optical analysis assembly for a liquid sample, comprising:
   a micro-structured substrate having a structure to support the liquid sample, the substrate comprising,
      a lower face;
      an upper face;
      at least one surface cavity, having a volume V0, opening onto said upper face and forming an analysis zone for the liquid sample;
      a first groove, having a first volume V1, arranged around each surface cavity and opening onto said upper face;
      at least one second groove opening on said upper face and arranged around the first groove;
      wherein a sum of volumes of the second grooves being equal to V2, a volume V1+V2 being greater than or equal to 0.05 V0, a depth of the first and second grooves being between 10 and 500 microns; and
      wherein the first and second grooves are continuous and not in a fluid communication with one another;
   at least one liquid sample arranged in said at least one surface cavity of the micro-structured substrate, a volume of the liquid sample being greater than a volume of said at least one surface cavity on which said at last one liquid sample is arranged;
   a cover slip covering the micro-structured substrate and said at least one liquid sample, closing all the cavities of the micro-structured substrate; and
   wherein the structure of the micro-structured substrate prevents generation of bubbles when closing the cavities with the cover slip.

19. A method of performing an optical analysis of a liquid sample using the micro-structure substrate according to claim 1.

20. A method of performing an optical analysis of a liquid sample using the optical analysis assembly according to claim 18.

21. The micro-structured substrate according to claim 1, wherein the grooves are microchannels of triangular or trapezoidal sections.

* * * * *